United States Patent [19]

Sinnreich et al.

[11] Patent Number: 5,079,008
[45] Date of Patent: Jan. 7, 1992

[54] TRANSDERMAL MONOLITH SYSTEMS

[75] Inventors: Joel Sinnreich, Basel; Peter Fankhauser, Ettingen, both of Switzerland

[73] Assignee: Ciba-Geigy Corporation, Ardsley, N.Y.

[21] Appl. No.: 547,538

[22] Filed: Jun. 29, 1990

Related U.S. Application Data

[63] Continuation of Ser. No. 337,996, Apr. 14, 1989, abandoned.

[30] Foreign Application Priority Data

Apr. 22, 1988 [CH] Switzerland .................. 1524/88

[51] Int. Cl.$^5$ .............................................. A61F 13/02
[52] U.S. Cl. .................................... 424/448; 424/449; 424/447; 514/946; 514/947
[58] Field of Search ...................... 424/448, 449, 447; 514/946, 947

[56] References Cited

U.S. PATENT DOCUMENTS

| | | | |
|---|---|---|---|
| 4,440,770 | 4/1984 | Mechida et al. | 424/258 |
| 4,440,777 | 4/1984 | Zupan | 424/45 |
| 4,560,553 | 12/1985 | Zupan | 424/78 |
| 4,623,346 | 11/1986 | von Bittera et al. | 604/896 |
| 4,627,852 | 12/1986 | von Bittera et al. | 604/897 |
| 4,668,232 | 5/1987 | Cordes et al. | 604/897 |
| 4,685,911 | 8/1987 | Konno et al. | 424/448 |
| 4,699,792 | 10/1987 | Nick et al. | 424/446 |
| 4,776,850 | 10/1988 | Guse et al. | 604/304 |
| 4,943,435 | 7/1990 | Baker et al. | 424/448 |

*Primary Examiner*—Thurman K. Page
*Assistant Examiner*—Leon Horne
*Attorney, Agent, or Firm*—JoAnn Villamizar

[57] ABSTRACT

The invention relates to a monolith transdermal therapeutic system for the delivery of permeable drugs, especially formoterol, in the form of a matrix system comprising three layers:

a) a backing layer which is impermeable to the components of the adhesive layer b), b) an adhesive layer capable of releasing the drug and consisting of a permeable polymeric material which is compatible with the skin and contains at least one drug which is capable of permeation across the skin, a combination of eucalyptol having a purity of at least 70% with an additional flux enhancer and further optional pharmaceutical excipients, and c) a protective release liner which can be peeled from the adhesive contact layer b).

7 Claims, No Drawings

TRANSDERMAL MONOLITH SYSTEMS

This application is a continuation of application Ser. No. 337,996, filed Apr. 14, 1989, now abandoned.

The present invention relates to a pharmaceutical monolith system for the transdermal application of skin-permeable drugs, to a process for the preparation of said monolith system and to the therapeutic use thereof for the prevention and treatment of various conditions and diseases.

The topical application of drugs by means of transdermal therapeutic systems is considered to be a particularly advantageous form of drug delivery whenever the oral, or another parenteral, dosage form would be detrimental and result, for example, in intolerance to, or side-effects of, the administered drug. Drug delivery by means of transdermal therapeutic systems is especially advantageous if a continuous release of the drug over a prolonged period of time is intended, or if drugs whose stability in the gastrointestinal tract would be insufficient are to have a systemic effect, by-passing the gastrointestinal tract.

Owing to the low permeability of the skin, especially of the stratum corneum, the drugs to be delivered transdermally must meet the following criteria:

1. in spite of the natural barrier of the stratum corneum, they must be sufficiently permeable to the skin to enter the bloodstream;
2. they must have good compatibility with the skin;
3. they must also be suitable for prophylactic or therapeutic long-term application or for substitution therapy (q.v. also H. Asche, Pharma International 4 (P), 1984, page 162).

These criteria limit the choice of drugs available for transdermal delivery, so that suitable therapeutic systems with only a few drugs have so far found use in therapy, for example with scopolamine, nitroglycerin, estradiol or clonidine.

It is known that the permeability of systemic drugs can be enhanced by means of so-called flux enhancers, for example dimethyl sulfoxide, dimethyl formamide or methyl n-dodecylsulfoxide, q.v. U.S. Pat. No. 3,257,864, 1-n-dodecylazacycloheptan-2-one, q.v. U.S. Pat. No. 4,316,893, or ethanol, q.v. German Offenlegungsschrift 3 205 258. The suitability of eucalyptol and mixtures thereof with other flux enhancers such as N-methyl-2-pyrrolidone, especially in the ratio of 1:1, to enhance the permeability of therapeutic agents in topical formulations such as creams, ointments, pastes, lotions and the like, is disclosed in European patent application 69 385.

In such topical formulations, the strongly fragrant eucalyptol may simply evaporate. Moreover, these formulations can only be applied for a short time, must therefore be frequently renewed, and, in general, permit only an inaccurate dosage of the drug.

It is the object of the present invention to provide an improved dosage form for the optical application of therapeutic agents in the form of a transdermal therapeutic system containing eucalyptol as flux enhancer.

This object is achieved by means of the present invention, which relates to a transdermal therapeutic system containing eucalyptol as flux enhancer in a solid matrix and having good stability and release properties.

The transdermal therapeutic system is in the form of a monolith system comprising the following components:

a) a backing layer which is impermeable to the components of the adhesive layer b),
b) an adhesive layer capable of releasing the drug and consisting of a permeable polymeric material which is compatible with the skin and contains at least one drug which is capable of permeation across the skin, a combination of eucalyptol having a purity of at least 70% with an additional flux enhancer and further optional pharmaceutical excipients, and
c) a protective release liner which can be peeled from the adhesive contact layer b).

The terms and definitions used throughout this specification have the following preferred meanings within the scope of the description.

The backing layer a) consists of a material or a combination of materials which must be impermeable to the components of the adhesive layer b), especially to liquid components of the formulation. It acts as a protective outer layer of the system. This backing layer may be made of high- or low-density polymers such as polyethylene, polypropylene, polyvinyl chloride, polyethylene terephthalate or also cellulose acetate or vinyl acetate/vinyl chloride copolymers and combinations thereof, preferably of composite films. An impermeable, flexible backing layer which fits snugly to the particular part of the body to which the transdermal system is attached is preferred.

The adhesive layer b) is located between the backing layer a) and the release liner c) and consists of a polymeric material which is compatible with the skin and is in the form of a matrix which contains the drug or a combination of drugs and, for enhancing penetration through the skin, a combination of eucalyptol and an additional flux enhancer and further optional excipients.

Suitable polymeric materials are permeable to the drug as well as to the combination of eucalyptol and the additional flux enhancer and, besides being compatible to the skin, have sufficient adhesiveness that the therapeutic system remains attached to the skin for at least one day and can subsequently be removed without exerting additional force. Further, suitable polymeric materials are dimensionally stable, despite the solvent properties of eucalyptol and the chemically pure 1,8-cineol.

Examples of such polymeric materials are silicone rubber (silicones), for example linear polysiloxanes in which the silicon atoms in the siloxane chain are substituted by two identical or different alkyl groups such as methyl or ethyl groups, aryl groups, for example phenyl groups, alkenyl groups such as vinyl or allyl groups, alkylaryl groups such as tolyl or xylyl groups, or alkyl groups, for example benzyl groups, and the terminal silicon atoms are substituted by three of the above organic radicals. The preparation of these silicones is disclosed in U.S. Pat. Nos. 2,541,137, 2,723,966, 2,863,846, 2,890,188, 2,927,907, 3,002,951 and 3,035,016. Silicones which are vulcanisable at room temperature are preferred.

Further suitable polymeric materials are hydrophilic polymers of monoesters of unsaturated carboxylic acids such as acrylic acid or methacrylic acid, for example the polyhydroxyethylacrylates or polyhydroxyethylmethacrylates thereof, the preparation of which is disclosed in U.S. Pat. Nos. 2,976,576 and 3,220,960, as well as copolymers of water-soluble aliphatic or cyclic vinyl amides, for example poly-N-vinylmethylacetamide, poly-N-vinylethylacetamide, poly-N-vinyl-methylpropionamide, poly-N-vinylethylpropionamide, poly-N-vinylmethyl-isobutyramide, poly-N-vinyl-2-pyrrolidone, poly-N-vinyl-2-piperidone, poly-N-vinyl-ε-caprolactam, poly-N-vinyl-5-methyl-2-pyrrolidone or poly-N-vinyl-3-methyl-2-pyrrolidone, preferably poly-N-vinylpyrrolidone having an average molecular weight of ca. 10,000 to 360,000, with water-soluble polyvinyl acetate or polyvinyl alcohol of different acetate content, for example polyvinyl acetate having a molecular weight of ca. 5,000 to 400,000 or polyvinyl alcohol having a degree of hydrolysis of ca. 85–98% and a degree of polymerization of ca. 500 to 2,500.

Preferred polymers are natural or synthetic rubber, for example polyisoprene, 1,4-butadiene polymer or polyisobutylene and mixtures thereof. Particularly preferred polymers are mixtures of different polyisobutylenes with different molecular weight ranges from ca. $1.0 \times 10^3$ to $5.0 \times 10^4$ and $1.0 \times 10^5$ to $5.0 \times 10^6$.

The drug for transdermal delivery is absorbed through the skin from the transdermal system of this invention in a therapeutically effective dose. It is possible to use all drugs which have a systemic effect and are capable of permeation across the skin and which are absorbed by the surface of the body to which the transdermal system is attached, observing known dosage particulars and directions for use. The dosage rates will depend on the drug to delivered. Suitable drugs which have a systemic effect are, for example, antibacterial agents such as penicillins, tetracyclins, oxytetracyclins, chlorotetracyclins, chloramphenicol or sulfonamides; sedatives and/or hypnotic drugs such as pentabarbitone sodium, phenobarbitone, secobarbitone sodium, codein, α-bromoisovaleryl urea, carbromal or sodium phenobarbitone; psychostimulants such as 3-(2-aminopropyl)indole acetate or 3-(2-aminobutyl)indole acetate; antihypertensives such as reserpine or clonidine; tranquilisers such as chloropromazine hydrochloride or thiopropazate hydrochloride; hormones such as adrenocorticosteroids, for example 6α-methylprednisoles; androgenic steroids, for example methyl testosterone and fluoxymesterone; estrogenic steroids, for example estrone, 17β-estradiol and ethynyl estradiol, progesterone or norethindrone, combinations of estrogens with synthetic gestagens or progesterones, for example 17β-estradiol with norethisterone-17-acetate or 17β-estradiol with progesterone; antipyretics such as acetylsalicyclic acid, morphine and other analgetics derived from morphine; vasodilators, for example nitroglycerin or isosorbide dinitrite; cardiac glycosides such as digitoxin or ouabain; beta-blockers such as propranolol, oxprenolol or metroprolol; anticholinergic drugs such as atropine, methscopolamine bromide, scopolamine, hyoscyamine or methscopolamine in combination with phenobarbitone; antimalerial drugs such as 4-aminoquinolines, 9-aminoquinolines or pyrimethamine; drugs for combating addictive habits, for example nicotine for combating addiction to smoking; broncholytic drugs such as formoterol; local anaesthetics such as tetracaine, nupercaine or lidocaine.

Particularly preferred drugs which are capable of permeation across the skin and which are present in the adhesive layer b) are nitroglycerin, scopolamine, formoterol, 17β-estradiol, progesterone, 17β-estradiol in combination with norethisterone acetate or progesterone, or lidocaine.

The above drugs, especially the preferred ones, may be present in the adhesive layer b) in the free form, for example as acid or as bases, or as pharmaceutically acceptable salts, for example as chloride, bromide, acetate, fumarate, maleate, succinate, lactate and the like.

The term "eucalyptol having a degree of purity of at least 70%" comprises formulations containing more than 70% to 100% of 1,8-cineol. In various pharmacopeias, formulations containing ca. 70–95% of 1,8-cineol are also designated as eucalyptus oils, whereas the term "eucalyptol" is used for formulations containing more than 95% of 1,8-cineol.

Eucalyptus oils are terpentine-containing essential oils which contain eucalyptol or 1,8-cineol as main constituent (more than 70%) and which can be isolated from leaves, roots or the bark of eucalyptus plants of the species Eucalyptus globulus (common eucalyptus tree), Eucalyptus maculata, Eucalyptus cladocalyx or Eucalyptus sideroxylon. By means of conventional purification methods, for example rectification, this eucalyptus oil can be further processed to chemically pure 1,8-cineol (more than 99% pure). The adhesive layer b) preferably contains this chemically pure 1,8-cineol together with an additional flux enhancer.

Flux enhancers, also known in the literature as penetration enhancers, accelerators or sorption promoters, have the property of permitting the passage of drugs through the skin that are in themselves impermeable to the skin, especially the stratum corneum which functions as a barrier, and of enhancing the permeability of drugs and so make possible the permeation and absorption of therapeutic amounts of the drug to be delivered.

The use of a combination of eucalyptol, preferably in the form of chemically pure 1,8-cineol, together with an additional flux enhancer, substantially increases the amount released and the rate of release (amount released per unit of time) of the drug contained in the adhesive layer b) or of a combination of drugs therein, and the corresponding absorption (or rate of absorption) through the skin. In addition to the drug itself or of a combination of drugs, sufficient amounts of the flux enhancer present in the system are released without the risk of irritating effects such as skin irritation or erythema, so that the permeability of the drug and penetration through the skin are enhanced and the absorption of sufficient amounts of drug into the bloodstream is ensured.

Examples of additional flux enhancers are monohydric saturated or unsaturated aliphatic, cycloaliphatic or aromatic alcohols of 1 to 12 carbon atoms, for example ethanol, isopropanol, n-hexanol or cyclohexanol; aliphatic, cycloaliphatic or aromatic hydrocarbons of 5 to 12 carbon atoms, for example hexane, cyclohexane, isopropyl benzene and the like; cycloaliphatic or aromatic aldehydes and ketones of 4 to 10 carbon atoms, for example cyclohexanone; amides such as acetamide, N,N-diethyl-m-toluamide, N,N-di-lower alkylacetamide such as N,N-dimethylacetamide or N,N-diethylacetamide, dimethyl propionamide; $C_{10}$–$C_{20}$alkanoylamides, for example N,N-dimethyllauroylamide, 1-n-$C_{10}$–$C_{20}$alkylazacycloheptan-2-one, for example 1-n-dodecylazacycloheptan-2-one (Azone®, Nelson), or N-2-hydroxyethylacetamide; N-alkyl-substituted cyclic amides, for example N-methyl-2-pyrrolidone; and also carriers and/or penetration enhancers such as aliphatic, cycloaliphatic and aromatic esters, for example isopropyl myristate, N,N-di-lower alkylsulfoxide, unsaturated oils, halogenated or nitrated aliphatic, cycloaliphatic hydrocarbons, salicylates, polyalkylene glycol silicates and mixtures thereof.

A combination of chemically pure 1,8-cineol with N-methyl-2-pyrrolidone is preferred, while a combination of 5 to 9.5 parts by weight of 1,8-cineol and suitably 5 to 0.5 parts by weight (based on 10 parts by weight) of N-methyl-2-pyrrolidone. Compared with pure N-methyl-2-pyrrolidone or 1,8-cineol, such combinations have the advantage that they can be processed with the polymeric material of the adhesive layer b), for example polyisobutylene mixtures, to homogeneous matrix systems of sufficient adhesiveness which are capable of drug release.

A combination of ca. 9 parts of chemically pure 1,8-cineol and 1 part by weight of N-methyl-2-pyrrolidone is especially preferred.

The adhesive layer c) may contain further optional excipients. Suitable excipients are water, isotonic aqueous saline solution, dextrose in water or saline solution, liquid glyceryl triesters with low molecular fatty acids, lower alkanols, natural oils such as corn oil, groundnut oil, sesame oil, castor oil and the condensates thereof with ethylene oxide and the like, hydrocarbons such as mineral oil of pharmaceutical quality, silicones, emulsifiers such as monoglycerides or diglycerides of fatty acids, phosphatidic acid derivatives such as lecithin or cephalin, polyalkyene glycols such as polyethylene glycol, aqueous phases to which a swelling agent such as sodium carboxymethyl cellulose has been added, sodium alginate, polyvinylpyrrolidone and the like, to which dispersants or emulsifiers such as lecithin may also be added, polyoxyethylene and the like. These excipients may contain further additives such as preservatives, stabilisers, wetting agents, emulsifiers and the like.

The removable protective release liner c) is peeled from the adhesive contact layer c) prior to application of the transdermal system. It is made of materials which are impermeable to the components of the adhesive layer c). The same materials may be used for the preparation of the release liner as for the preparation of the backing layer a), as well as metal foils, for example aluminium foil. Organic polymers can be made removable by suitable surface treatment, for example by siliconising them.

The present invention preferably relates to a monolith transdermal therapeutic system comprising at least three layers:

a) a backing layer which is impermeable to the components of the adhesive layer b), b) an adhesive layer capable of drug release and consisting of different polyisobutylenes having different molecular weight ranges from ca. $1.0 \times 10^3$ to $5.0 \times 10^4$ and $1.0 \times 10^5$ to $5.0 \times 10^6$, which layer contains a permeable drug, a combination of ca. 5 to 9.5 parts by weight of 1,8-cineol and suitably 0.5 to 5 parts by weight of N-methyl-2-pyrrolidone and further optional pharmaceutical excipients, and c) a protective release liner which can be removed from the adhesive layer c).

The invention relates first and foremost to a monolith transdermal therapeutic system for the transdermal delivery of formoterol comprising at least three layers:

a) a backing layer which is impermeable to the components of the adhesive layer b), b) an adhesive layer capable of drug release and consisting of different polyisobutylenes having different molecular weight ranges from ca. $1.0 \times 10^3$ to $5.0 \times 10^4$ and $1.0 \times 10^5$ to $5.0 \times 10^6$, which layer contains a permeable drug selected from nitroglycerin, scopolamine, formoterol, $17\beta$-estradiol, progesterone, $17\beta$-estradiol in combination with norethisterone acetate or progesterone or lidocaine, or a combination of said drugs, a combination of 9 parts by weight of 1,8-cineol and 1 part by weight of N-methyl-2-pyrrolidone and further optional pharmaceutical excipients, and c) a protective release liner which can be removed from the adhesive layer c).

The transdermal therapeutic system of this invention is prepared by applying the adhesive layer b) with its components to the removable protective release liner c) and then applying the backing layer a) or, conversely, applying the adhesive layer b) to the backing layer a) and then applying the protective release liner c) and, after carrying out one of these two variants, combining the different layers and bringing the monolith system into the desired form. This is done by punching the monolith from the laminate. If desired, the adhesive layer b) is bonded to the backing layer a), using additional adhesive material. The different layers can also be heat-sealed.

The preparatory methods and utilities are disclosed in U.S. Pat. Nos. 3,598,122, 3,598,123, 3,797,494 and 4,060,084, preferably in German Offenlegungsschrift specifications 2 604 718 and 3 205 258 and in U.S. Pat. Nos. 4,031,894 and 4,262,003, or in the publication of H. Asche in Schweiz. Rundschau Med. (Praxis) 74, No. 11, 257-260 (1985) relating to the preparation of matrix or monolith systems, although the utility of this invention is not limited to the transdermal therapeutic systems described in these publications.

EXAMPLE 1 a) Preparation of the Adhesive Layer

The components of the adhesive layer are formulated to a uniform composition in amounts of 30 g by mixing in a kneader which is capable of processing highly viscous pastes, for example EVA 153, Brabender, at an operating temperature of 60° C. First, 7.5 g of polyisobutylene having an average molecular weight of ca. $1.3 \times 10^6$ (Oppanol ® B-100, BASF) is kneaded for 5 minutes and then 7.5 g of polyisobutylene having an average molecular weight of ca. $4.0 \times 10^4$ (Oppanol B-10) are added. The viscous mixture is kneaded for 5 minutes. A solution of 60 mg of formoterol in 1.5 g of N-methyl-2-pyrrolidone and 13.5 g of 1,8-cineol are then added, with the optional addition of an antioxidant (Irganox ® 1010, Ciba-Geigy), and kneading is continued for 30 minutes. After cooling, the formulation is weighted to determine possible weight losses.

b) Preparation of the Monolith System

Monolith systems can be prepared by using a heatable laboratory press (Jauch) at an operating temperature of ca. 60°-80° C. This is done by applying 3.2 g of the formation prepared according to Example 1a) with formoterol base to a ca. 1 mm aluminised polyester sheet which is held in place by a metal frame having a $3 \times 8$ cm aperture.

The formulation is covered with a sheet of siliconised polyester and the resultant laminate is pressed under a pressure of ca. 6 bar for about 30 seconds at a temperature below 60° C. Monoliths of suitable size, for example having a diameter of ca. 2.6 cm, can subsequently be punched from the laminate.

To prepare monoliths with a particularly thin adhesive layer (less than 50μ in diameter), the components of the adhesive layer are dissolved in heptane and the solution is sprayed on to the backing layer of aluminised polyester, such that a monolith layer of the desired thickness is obtained after evaporation of the solvent. The other process steps are the same.

EXAMPLE 2

Test procedure

A piece of pig epidermis measuring ca. $3 \times 3$ cm$^3$ is mounted in a diffusion cell in accordance with the method of T. J. Franz described in Invest. Dermatol. 64, 190–195 (1975). In the lower acceptor compartment, isotonic buffer solution of pH 7.4 and, in the upper donor compartment, the transdermal therapeutic system of Example 1, are brought into contact with the pigskin (ca. 5 cm$^2$) which is held fast between donor and acceptor compartment. An aliquot of the aqueous acceptor solution from the acceptor compartment is inspected after 24 hours for the concentration of formoterol, and the rate of flux of formoterol [ng/cm$^2$·h] is determined therefrom over periods of 0–4 hours, 7–24 hours and 24–48 hours, as well as the total amounts released by the system (=cumulated permeation in μg/cm$^2$) after 24 and 48 hours.

| t [h] | rate of flux [ng/cm$^2$.h] |
| --- | --- |
| 0–4 | 74 |
| 7–24 | 309 |
| 2–48 | 1026 |
| | cumulated permeation [μg/cm$^2$] |
| 24 | 5.8 |
| 48 | 30.3 |

EXAMPLE 3

In accordance with the procedures described in Examples 1a) and 1b), a laminate is prepared whose adhesive layer contains the following components:

| | |
| --- | --- |
| polyisobutylene OPPANOL B-100 | 6.30 g |
| polyisobutylene OPPANOL B-10 | 10.00 g |
| N-methyl-2-pyrrolidone | 0.90 g |
| 1,8-cineol | 7.80 g |
| 17β-estradiol | 0.12 g |
| progesterone | 0.25 g |
| | 25.37 g |

Disc-shaped monoliths having a diameter of ca. 2.8 cm are punched from the laminate.

EXAMPLE 4 a) In accordance with the procedures described in Examples 1a) and 1b), a laminate is prepared whose adhesive layer contains the following components:

| | |
| --- | --- |
| polyisobutylene OPPANOL B-100 | 6.30 g |
| polyisobutylene OPPANOL B-10 | 10.00 g |
| N-methyl-2-pyrrolidone | 0.90 g |
| 1,8-cineol | 7.80 g |
| 17β-estradiol | 0.12 g |
| | 25.12 g | b) In accordance with the procedure described in Example 2, the rate of flux of 17β-estradiol is measured over periods of 0–6, 6–24 and 24–48 hours:

| t [h] | rate of flux [μg/cm$^2$.h] |
| --- | --- |
| 0–6 | 1.02 |
| 6–24 | 0.82 |
| 24–48 | 0.58 |

EXAMPLE 5 a) In accordance with the procedures described in Example 1a) and 1b), a laminate is prepared whose adhesive layer contains the following components:

| | |
| --- | --- |
| polyisobutylene OPPANOL B-100 | 6.28 g |
| polyisobutylene OPPANOL B-10 | 9.97 g |
| 1,8-cineol | 7.87 g |
| N-methyl-2-pyrrolidone | 0.88 g |
| progesterone | 0.25 g |
| | 25.25 g |

Disc-shaped monoliths having a diameter of ca. 2.8 cm are punched from the laminate.

b) In accordance with the procedure described in Example 2, the rate of flux of progesterone is measured over periods of 0–4, 4–7, 7–24 and 24–48 hours:

| t [h] | rate of flux [μg/cm$^2$.h] |
| --- | --- |
| 0–4 | 3.09 |
| 4–7 | 3.27 |
| 7–24 | 2.51 |
| 24–48 | 2.08 |

EXAMPLE 6 a) Preparation of the Adhesive Layer

The components of the adhesive layer are processed in amounts of 30 g by mixing in a kneader, for example a Brabender PLE 651. At a temperature of 60°, 60.2 g of polyisobutylene having an average molecular weight of ca. $1.3 \times 10^6$ (OPPANOL B-100) are kneaded. After kneading for 5 minutes, 76.0 g of polyisobutylene having an average molecular weight of ca. $4.0 \times 10^4$ (OPPANOL B-10) are added. Kneading is continued again for 5 minutes and then 66.4 g of polyisobutylene having an average molecular weight of ca. $8.0 \times 10^2$ (OPPANOL B-3) are added. This mixture is kneaded for 5 minutes. A solution of 30 g of lidocaine base in 5.5 g of N-methyl-2-pyrrolidone, 49.1 g of 1,8-cineol and 12.8 g of paraffin oil are then added and the entire mixture is processed to a homogeneous formulation for 25 minutes.

b) Preparation of the Monolith Systems

In accordance with Example 1, monoliths of different sizes, for example 14 cm$^2$, 26 cm$^2$, 37 cm$^2$ and 85 cm$^2$ are prepared. A polyester sheet is used as backing layer.

What is claimed is:

1. A monolith transdermal therapeutic system comprising
   a) a backing layer which is impermeable to the components of the adhesive layer b),
   b) an adhesive monolithic matrix layer consisting of a mixture of different polyisobutylenes having different molecular weight ranges, of $1.0 \times 10^3$ to $5.0 \times 10^4$ and $1.0 \times 10^5$ to $5.0 \times 10^6$ as the permeable polymeric material which is compatible with the skin and which contains at least one drug which is capable of permeation across the skin, a combination of 1,8-cineol having a degree of purity of at least 70% and N-methyl-2-pyrrolidone and further optional pharmaceutical excipients, and c) a protective release liner which can be peeled off from the adhesive contact layer b).

2. A monolith transdermal therapeutic system according to claim 1, wherein the adhesive monolithic matrix layer b) contains a combination of 1,8-cineol having a degree of purity greater than 99% and N-methyl-2-pyrrolidone.

3. A monolith transdermal therapeutic system according to claim 1, wherein the combination of 1,8-cineol and N-methyl-2-pyrrolidone contains 5 to 9.5 parts by weight of 1,8-cineol and 5 to 0.5 parts by weight (based on 10 parts by weight) of N-methyl-2-pyrrolidone.

4. A monolith transdermal therapeutic system according to claim 3, wherein the combination of 1,8-cineol and N-methyl-2-pyrrolidone contains ca. 9 parts by weight of 1,8-cineol and 1 part by weight of N-methyl-2-pyrrolidone.

5. A monolith transdermal therapeutic system according to claim 1, wherein the adhesive monolithic matrix layer b) contains a permeable drug selected from the group consisting of nitroglycerin, scopolamine, formoterol, 17$\beta$-estradiol, progesterone and lidocaine.

6. A monolith transdermal therapeutic system according to claim 1, wherein the adhesive monolithic matrix layer b) contains a combination of 17$\beta$-estradiol with norethisterone-7-acetate or of progesterone with 17$\beta$-estradiol.

7. A monolith transdermal therapeutic system according to claim 1, comprising at least three layers:

a) a backing layer which is impermeable to the components of the adhesive layer b), b) an adhesive monolithic matrix layer capable of drug release and consisting of different polyisobutylenes having different molecular weight ranges from $1.0 \times 10^3$ to $5.0 \times 10^4$ and $1.0 \times 10^5$ to $5.0 \times 10^6$, which layer contains a permeable drug selected from nitroglycerin, scopolamine, formoterol, 17$\beta$-estradiol, progesterone, 17$\beta$-estradiol in combination with norethisterone acetate or progesterone or lidocaine, a combination of 9 parts by weight of 1,8-cineol and 1 part by weight of N-methyl-2-pyrrolidone and further optional pharmaceutical excipients, and c) a protective release liner which can be removed from the adhesive layer.

* * * * *